United States Patent
Bruder et al.

(10) Patent No.: US 6,391,612 B1
(45) Date of Patent: May 21, 2002

(54) VECTORS, CELLS, AND METHODS FOR THE PRODUCTION OF DELETERIOUS ADENOVIRAL, HERPES VIRAL AND ADENO-ASSOCIATED VIRAL VECTORS

(75) Inventors: Joseph T. Bruder, Ijamsville; Imre Kovesdi, Rockville; Alena Lizonova, Gaithersburg, all of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/428,507

(22) Filed: Oct. 27, 1999

Related U.S. Application Data

(63) Continuation of application No. PCT/US99/02889, filed on Feb. 11, 1999.
(60) Provisional application No. 60/074,372, filed on Feb. 11, 1998.

(51) Int. Cl.[7] .......................... C12P 19/34; C12N 15/00; C12N 5/00; C12N 7/01; C07H 21/04
(52) U.S. Cl. ............................... 435/235.1; 435/320.1; 435/91.33; 435/325; 435/410; 536/23.1
(58) Field of Search .......................... 435/91.33, 320.1, 435/325, 235.1, 410; 536/23.1

(56) References Cited

U.S. PATENT DOCUMENTS

| | | | |
|---|---|---|---|
| 5,443,964 A | | 8/1995 | Pickup et al. |
| 5,843,723 A | * | 12/1998 | Dubensky et al. ......... 435/69.3 |
| 6,204,052 B1 | * | 3/2001 | Bout et al. ............... 435/320.1 |

FOREIGN PATENT DOCUMENTS

| | | |
|---|---|---|
| WO | WO 95/00160 | 1/1995 |
| WO | PCT 96/01902 A | 1/1996 |
| WO | WO 97/33606 | 3/1996 |
| WO | WO 96/25501 | 8/1996 |
| WO | WO 97/10006 | 9/1996 |
| WO | PCT 97/03998 A | 2/1997 |
| WO | WO 97/23501 | 7/1997 |
| WO | PCT 99/13073 A | 3/1999 |

OTHER PUBLICATIONS

Cohen, *Biochemical Journal*, 326, 1–6 (1997).
Shinoura et al., *Human Gene Therapy*, 9 (18), 2683–2689 (Dec. 1998).
Talley et al., *Molecular and Cellular Biology*, 15 (5), 2359–2366 (May 1995).
Thome et al., *Nature*, 386, 517–519 (Apr. 1997).
Bleackley et al., "Inhibition of Cell Mediated Cytotoxicity by Viral Proteins," Abstracts from the First University of Alberta Gene Therapy Meeting, Nov. 23, 1995 (http://www.ualberta.ca/~britchie/abstracts.html).
Brockman et al., *Mol. Cell Biol.*, 15, 2809–2818 (1995).
Bruder et al., *Genes and Development*, 6, 545–556 (1992).
Chen et al., Abstracts of Papers Presented at The Meeting on Programmed Cell Death, Cold Spring Harbor, NY, p. 250, (Sep. 1997).
Chen et al., *J. Biol. Chem.* 273 (10), 5815–5820 (1998).
Clem et al., *Cell Biology*, 7, 337–339 (1997).
*Derwent World Patents Index*, WPI Accession No. 97–380167 (Derwent Week 199735), JP-A-9163982 (Hisamitsu Pharm Co Ltd) (Jun. 24, 1997).
Gooding et al., *Cell*, 53, 341–346 (1988).
Levine et al., *Nature*, 361, 739–742 (1993).
Macen et al., *PNAS USA*, 93, 9108–9113 (1996).
Nava et al., *J. Virology*, 72 (1), 452–459 (1998).
Nicholson et al., *Trends in Biological Sciences (TIBS)*, 22, 299–306 (1997).
Patel et al., *PNAS USA*, 85, 9431–9435 (1988).
Pickup et al., *PNAS USA*, 83, 7698–7702 (1986).
Ray et al., *Cell*, 69, 597–604 (1992).
Telling et al., *J. Virol.*, 68 (1), 541–547 (1994).
Tewari et al., *J. Biol. Chem.* 270 (7), 3255–3260 (1996).
White, *Genes & Development*, 10, 1–15 (1996).

\* cited by examiner

Primary Examiner—David Guzo
Assistant Examiner—Gerald G. Leffers, Jr.
(74) *Attorney, Agent, or Firm*—Leydig, Voit & Mayer, Ltd.

(57) ABSTRACT

The present invention provides a method of in vitro propagation of a viral eukaryotic gene transfer vector comprising a deleterious, i.e., a cytostatic, cytotoxic, or apoptotic, gene in a eukaryotic, e.g., a mammalian, host-production cell, comprising a blocking gene. The blocking gene inhibits the adverse effects of the deleterious gene on the eukaryotic host-production cell. Vectors and cells useful in the context of the present inventive method are also provided.

25 Claims, 4 Drawing Sheets

VECTORS, CELLS, AND METHODS FOR THE PRODUCTION OF DELETERIOUS ADENOVIRAL, HERPES VIRAL AND ADENO-ASSOCIATED VIRAL VECTORS

CROSS REFERENCE TO RELATED APPLICATIONS

This application claims priority under 35 U.S.C. §120 to International Application No. PCT/US99/02889, filed on Feb. 11, 1999, which claims priority under 35 U.S.C. §119(e) to U.S. provisional application No. 60/074,372, filed Feb. 11, 1998.

TECHNICAL FIELD OF THE INVENTION

The present invention relates to vectors, cells and methods useful for making viral eukaryotic gene transfer vectors.

BACKGROUND OF THE INVENTION

Viral eukaryotic gene transfer vectors have a variety of utilities from the in vitro and in vivo study of cell biology to clinical therapies that alleviate medical conditions. These viral vectors usually must be propagated in a host cell line in vitro prior to use experimentally, clinically, or otherwise. However, some vector designs are not produced efficiently, or are not produced at all, in the host cell line. In some instances, the virus that forms the basis of the viral vector can be so virulent that it efficiently kills the host cells at low or moderate multiplicities of infection (MOI; a low or moderate MOI is an MOI of about 0.1 to about 5 pfu/cell and about 3 to about 20 pfu/cell, respectively) and the viral vector is not effectively replicated in vitro.

In other instances, one or more passenger genes carried by these vectors can cause them to be substantially more cytostatic, cytotoxic, or apoptotic to eukaryotic host cells. In these cases, it has been shown that the passenger gene carried by the viral vector is primarily responsible for the poor production characteristics of these vectors since similar vectors that lack passenger genes are produced efficiently. Moreover, the transduction of eukaryotic cells with viral eukaryotic gene transfer vectors can seriously impede the host cell's metabolism independently of the passenger gene. When the deleterious effects of the passenger gene act in concert with the deleterious effects of transduction by the gene transfer vector, the cell can be compromised to the extent that few or no gene transfer vectors are produced. Many of the most useful viral eukaryotic gene transfer vectors currently contemplated in the art fit this description.

One result of the transduction of a viral gene transfer vector comprising a deleterious gene into a host cell can be the apoptosis of the host cell. The term "apoptosis" is well understood in the biological arts and is characterized by a number of phenomena, including "cytoplasmic boiling," severe chromatin condensation and chromosomal fragmentation. It is known that many eukaryotic viruses carry anti-apoptotic genes that facilitate survival of the host cell until viral replication has proceeded to an extent sufficient to ensure the propagation of the virus (e.g., the 19K E1B product of adenoviruses). Nevertheless, viral eukaryotic gene transfer vectors, in particular adenoviral vectors, comprising certain passenger genes lack the capacity to prevent rapid and severe apoptotic responses such that no yield or poor yields of the desired vector are obtained by passaging on typical host cells.

Therefore, there exists a need for a better method of producing cytostatic, cytotoxic, or apoptotic vectors in eukaryotic host cells, particularly those comprising passenger genes that strongly induce these effects. The present invention provides vectors and cells for the production of viral eukaryotic gene transfer vectors that comprise a passenger gene that diminishes the yield of the viral vector because the passenger gene product is cytotoxic or cytostatic, or induces the apoptosis of a host cell for the viral vector. The present invention also provides methods of producing such vectors. These and other advantages of the present invention, as well as additional inventive features, will be apparent from the description of the invention and examples provided herein.

BRIEF SUMMARY OF THE INVENTION

The present invention provides a method of producing in vitro a viral eukaryotic gene transfer vector, particularly an adenoviral vector, that is deleterious itself, or comprises a deleterious gene, e.g., a cytostatic, cytotoxic, or apoptotic gene. The method comprises inhibiting the deleterious effects of the viral eukaryotic gene transfer vector or the deleterious gene of which it is comprised on eukaryotic, e.g., mammalian, host cells by expressing in the host cells a blocking gene that blocks the deleterious effects of the viral eukaryotic gene transfer vector or the deleterious gene of which it is comprised. The blocking gene can be part of the host cell (e.g., integrated into the host cell genome or present on a plasmid or vector) or the viral eukaryotic gene transfer vector. Accordingly, the present invention also provides novel cells and viral eukaryotic gene transfer vectors. The invention may best be understood in the following detailed description of the preferred embodiments.

DETAILED DESCRIPTION OF THE INVENTION

Figure 1:
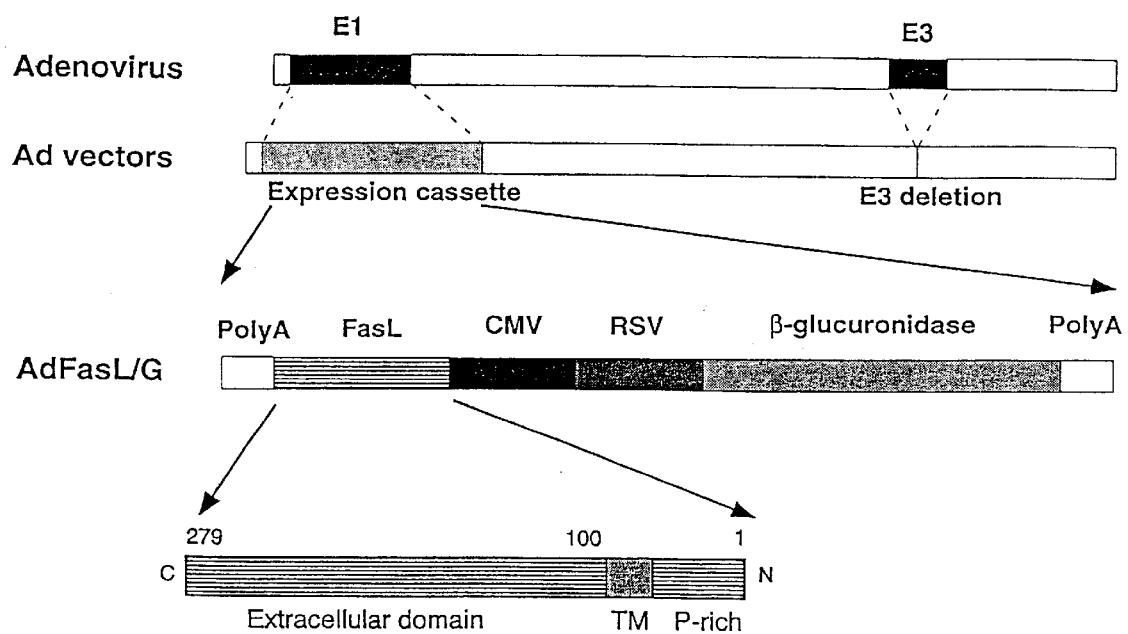
FIG. 1 is a schematic diagram of the generation of the adenoviral vector AdFasL/G.

Viral eukaryotic gene transfer vectors can be made or propagated in vitro in host cells that are permissive for their replication and that complement any defects in essential gene functions of the viral vector ("host-production cells"). However, certain viral eukaryotic gene transfer vectors are highly cytotoxic to the host cells, or strongly induce the cytostasis or, particularly, the apoptosis of the host cells. Such vectors are described herein as being "derived from deleterious viruses" and are referred to herein as "deleterious viral eukaryotic gene transfer vectors" or "deleterious vectors." Frequently, it is the passenger gene carried by the viral eukaryotic gene transfer vector that encodes a gene product (i.e., an RNA or protein, preferably a protein) that decreases the efficiency of propagation of the vector, or blocks propagation of the vector altogether. Such genes are referred to herein as "deleterious genes."

Surprisingly, it has been found that the adverse effects of the deleterious viral eukaryotic gene transfer vector or the deleterious gene carried by the viral eukaryotic gene transfer vector on the production (peak yield per cell) of the viral eukaryotic gene transfer vector can be substantially mitigated by providing within the host-production cell a gene product that blocks the adverse effects of vector-directed gene expression. Accordingly, the present invention provides a method of enhancing the production or peak yield of a deleterious viral eukaryotic gene transfer vector, e.g., a cytotoxic, cytostatic or apoptotic viral eukaryotic gene transfer vector. For the purposes of the present invention, a gene that encodes a gene product that is cytotoxic or induces the cytostasis or apoptosis of a host-production cell is a "deleterious gene," whereas the gene product is a "deleterious gene product." A gene that blocks the adverse effects of a deleterious vector or a deleterious gene is a "blocking gene," whereas the gene product is a "blocking gene product."

When a deleterious gene is expressed in the context of a viral eukaryotic vector, the effect of the deleterious gene can be significantly amplified as a result of viral gene expression. Surprisingly, the present invention provides a method of enhancing the production of a viral eukaryotic gene transfer vector that carries a deleterious gene that causes the vector to be produced inefficiently in ordinary host-production cells (relative to nearly identical vectors that do not express the deleterious gene). The expression of a blocking gene product in a host-production cell suitably enhances the peak yield of the viral eukaryotic gene transfer vector in vitro.

The present inventive method comprises introducing a viral eukaryotic gene transfer vector of the type described above into a host-production cell comprising a blocking gene. The present inventive method is independent of the manner in which the blocking gene is introduced into the host-production cell. For example, the blocking gene can be incorporated into the genome of the host-production cell, introduced into the host-production cell on the viral eukaryotic gene transfer vector, or introduced into the host-production cell on a separate vector or plasmid. Methods of introduction are known in the art and include, but are not limited to, transduction and transfection. The blocking gene can be incorporated/introduced into the host-production cell prior to, or at substantially the same time as, the viral eukaryotic gene transfer vector. If the blocking gene product is introduced into the host-production cell after the viral eukaryotic gene transfer vector, it should be introduced as soon as possible, i.e., immediately.

The viral eukaryotic gene transfer vector produced in the present inventive method can comprise any suitable viral eukaryotic vector. Suitable viral eukaryotic vectors include, but are not limited to, adenoviral vectors, adeno-associated vectors and herpes viral vectors. Other suitable vectors include retroviral vectors. The vector is preferably a DNA viral vector, especially an adenoviral vector. Moreover, the vector preferably comprises the minimal essential elements for viral replication and packaging in te presence of a helper virus (i.e., a viral amplicon, which ordinarily comprises a left and a right ITR or LTR and an encapsidation site).

Additionally, the viral eukaryotic gene transfer vector produced in the present inventive method can be designed to facilitate the present inventive method. For example, the viral eukaryotic gene transfer vector can comprise the blocking gene. For example, the viral eukaryotic gene transfer vector can be an adenoviral vector, which can be deleterious or comprises a deleterious gene and which comprises an anti-apoptotic gene as the blocking gene.

The blocking gene can be any suitable gene and can be derived from a viral or cellular source. If present on the viral eukaryotic gene transfer vector or another viral vector, preferably, the blocking gene is under the control of a heterologous promoter or is placed in a new trancriptional control unit within the virus. If present on a plasmid or in the genome of the eukaryotic host-production cell, the blocking gene can comprise a native promoter or a heterologous promoter a long as the promoter effects expression of the blocking gene coding sequence. In any event, the blocking gene desirably substantially blocks the deleterious effects on the host-production cell. Examples of blocking genes include, but are not limited to, genes that encode crmA, a caspase inhibitor such as baculoviral p35 or an IAP gene product, a FLIP gene product, and adenoviral 14.7 K protein. For example, with an adenoviral vector, the DNA encoding the 14.7 K protein is preferably moved from its native location in the E3 region to the E1 or E4 region of the adenoviral genome. It is also useful to link operably the DNA encoding the, 14.7 K protein to a more powerful or more regulatable promoter than the native E3 promoter. In this regard, any suitable promoter, e.g., the cytomegalovirus (CMV) immediate early promoter or a host-production cell restricted promoter, can be used to drive the expression of the 14.7 K protein.

Any of the present inventive vectors can be transiently or stably maintained in a cell to provide a novel cell or cell line. The novel cell or cell line is preferably mammalian.

The deleterious gene can be any suitable gene of interest. Examples of deleterious genes includes genes that encode FasL, FADD, or FLICE, other caspases, IκB, adenoviral E4/ORF4, adenoviral E1A products, TNF receptor, TRAIL receptor, Bcl-Xs, DR5 and RAID.

The host-production cell can be any cell (in vitro) that supports the replication of the desired viral eukaryotic gene transfer vector. Preferably, the host-production cell is eukaryotic, more preferably, the host-production cell is mammalian.

The deleterious effects of any particular gene product can vary from host-production cell to host-production cell. Accordingly, for the purposes of the present invention, the deleterious effect of a deleterious gene product is defined by the action of the gene product on a cell commonly used to propagate viral vectors. A preferred cell line in which to measure such deleterious effects is the HEK-293 cell line. A more preferred cell line is the AE25 cell line, which is an A549-based cell line that expresses the adenovirus type 2 early region I.

In the context of the present invention, a gene product that induces the apoptosis of a host-production cell preferably induces apoptosis of at least about 60% of the transfected cells in a population of HEK-293 cells transfected by CaPO$_4$ coprecipitation under ordinary conditions (i.e., those recommended by the ATCC for growth and propagation of cells at 50–60% confluence on a 10 cm diameter tissue culture plate) with 10 μg of pcDNA3.1 (Invitrogen, Carlsbad, Calif.) carrying the putative apoptotic gene under the control of a CMV immediate early promoter operably linked to the deleterious gene within 24 hrs of transfection. One skilled in the art will appreciate that, in any population of cells which have been transfected with a viral eukaryotic gene transfer vector, the number of cells that actually take up and express the transferred gene is usually substantially less than 100%. Accordingly, the skilled artisan will "control for" (i.e., take steps to measure) the transfection efficiency and will also make adjustments in the calculation of experimental results that pertain to transfection efficiency.

Similarly, a cytostatic gene in the context of the present invention reduces the tritiated-thymidine incorporation of actively dividing HEK-293 cells transfected with the gene preferably by more than about 75%, and more preferably by more than about 90%, under ordinary conditions. A cytotoxic gene in the context of the present invention is one that causes preferably at least about 75%, and more preferably at least about 90%, of the transfected HEK-293 cells to take up a vital stain (e.g., trypan blue), which is ordinarily excluded by viable cells, within 24 hrs of transfection.

In another embodiment, the present invention provides a eukaryotic cell useful in the production of a deleterious viral eukaryotic gene transfer vector. The present inventive cell comprises a gene that encodes and expresses a gene product that complements for at least one essential gene function of a eukaryotic virus and a blocking gene, as described above. Optionally, either or both genes can be stably incorporated into the genome to provide a cell line. For example, the cell can comprise genes encoding and expressing one or more essential gene functions of the E1 and E4 regions of an adenovirus and a blocking gene. These genes can be operably linked to any suitable promoter, including highly regulatable promoters, such as the sheep metallothionein promoter and the control region and promoter of the Tet expression system.

The present inventive host-production cell further comprises a viral eukaryotic gene transfer vector, e.g., an adenovirus. The viral eukaryotic gene transfer vector can comprise a deleterious gene. Alternatively, the viral eukaryotic gene transfer vector can comprise a non-deleterious gene, in which case the mere presence and replication of the viral eukaryotic gene transfer vector in the eukaryotic, preferably mammalian, host-production cell is deleterious to the host-production cell.

Advantageously, the present inventive host-production cell has an enhanced ability to provide peak yields of the viral eukaryotic gene transfer vector. For example, an adenovirus that carries a gene that encodes and expresses the Fas ligand in the cell (e.g., AdFasL/G, see FIG. 1) will preferably be produced at levels that are at least about five-fold greater in the present inventive host-production cell comprising a blocking gene than the peak yield that would be obtained from an otherwise identical host-production cell that does not comprise the blocking gene. Preferably, the cell would also provide at least about 200 pfu/cell through routine passage of AdFasL/G on the cell.

One embodiment of the present inventive host-production cell provided by the present invention is illustrated by, but not limited to, a modification of HEK-293 cells. HEK-293 cells contain a large adenoviral DNA segment that expresses the essential gene products of the E1 region of the adenoviral genome. HEK-293 cells are transduced or transfected with a gene that encodes and expresses a blocking gene product, such as crmA, which enhances the yield of a replication-deficient adenoviral gene transfer vector (e.g., lacking the E1 region of the adenoviral genome) carrying a deleterious gene. The eukaryotic cell, therefore, allows a substantial increase (i.e., preferably at least about a 5-fold, more preferably at least about a 20-fold, increase) in the production of a desired vector.

Examples of host-production cells in accordance with the present invention include, but are not limited to, any of the following cells that comprise two or more essential gene functions of a eukaryotic (in particular an adenoviral) vector and also comprise a blocking gene, such as crmA: AE25 cells (which are A549-based cells that express the adenovirus type 2 early region I), HEK-293/ORF6 cells (which are HEK-293 cells comprising a gene that inducibly expresses the adenoviral open reading frame 6 of the E4 region of the adenoviral genome), HEK-293/ORF6/E2A cells (which are HEK293/ORF6 cells that inducibly express the essential gene products of the E2A region of the adenoviral genome), A549/E1 cells (which are A549 cells that express the essential gene functions of the E1 region of the adenoviral genome), A549/E1/ORF6 cells, 911 retinoblastoma cells (Introgen), PER.C6 cells (Introgen), HEL/E1 cells (HEL cells expressing the E1 region of the adenoviral genome), as well as modifications of these cells and similar cells.

The expression of the blocking gene increases the yield of deleterious viral eukaryotic gene transfer vectors per host-production cell when compared to the yield of vectors per cell when the blocking gene is not expressed in the host-production cell. The blocking gene product preferably increases the yield of vector at least about 5-fold, and more, preferably increases the yield at least about 20-fold. In the absence of the blocking gene, many vectors are produced at less than 80 vectors per cell, some are produced at less than 20 vectors per cell, and others are produced at levels too low to quantify. In contrast, in the presence of the blocking gene, it is possible to obtain more than 200, 500, or 1,000 viral eukaryotic gene transfer vectors per cell.

Blocking genes that are useful in the context of the present invention are those that encode and express a gene product that directs the expression of a protein that inhibits a caspase. Caspase inhibitors, which are well-known in the art, are reviewed by Nicholson et al., *Trends Biol. Sci. (TIBS)*, 22, 299–306 (1997). The blocking gene product can directly inhibit the caspase or can function by acting on other points in the caspase pathway. The caspase inhibitor preferably inhibits the caspase protease by binding directly to the caspase. More preferably, the caspase inhibitor binds to a region of the caspase that comprises the protease cleavage site. Examples of caspase inhibitors useful in the context of the present invention include crmA, adenoviral 14.7 K protein, baculoviral p35 protein, IAP gene products and FLIP gene products. Adenoviral 14.7 K protein, baculoviral p35 protein and especially crmA are particularly useful in the context of the present invention.

IAP genes are well-known in the art and are reviewed by Clem et al., *Trends In Cell Biology*, 7, 337–339 (1997). IAP genes can be identified, inter alia, by the presence of two or more imperfect 65 amino acid repeats known as BIR motifs (see Clem et al., supra). IAP genes also possess a RING motif. Viral IAP genes tend to require the presence of the RING motif for anti-apoptotic activity; the cellular IAP genes preferably have the RING motif removed through genetic engineering procedures. As reported in Clem et al., the reason for this difference between cellular and viral IAP genes is unclear, but may be related to the fact that viral IAP genes tend to have fewer amino acids separating the BIR motifs and the RING domain. Irrespective of whether the IAP is viral or cellular, those IAP genes that most strongly inhibit apoptosis, including those which have their RING motifs deleted, are preferred in the context of the present invention.

FLIP genes are also well-known in the art and include, for example, those encoding *Molluscum contagiosum* virus proteins MC159 and MC160, equine herpes virus 2 protein E8, Casper and CASH. Similarly, the skilled artisan can readily identify baculoviral p35 genes, crmA and adenoviral 14.7 K protein.

In certain embodiments of the present invention, it can be demonstrated in a variety of ways that the blocking gene product facilitates the increase in vector production primarily by blocking the adverse effects of deleterious gene expression. For example, the deleterious gene can be mutated to contain a frameshift mutation in the DNA encoding an N-terminal portion of the protein (e.g., the seventh to tenth amino acid of the deleterious gene product) to generate a "frameshift vector". The frameshift vector can be evaluated in a "test-cell." A test cell is identical to the cell of the present invention, except that it does not contain the blocking gene. If the ratio of the peak yield of frameshift vectors per test-cell to the peak yield of non-frameshift vectors per test-cell is preferably at least about 5, more preferably at least about 20, then expression of the deleterious gene adversely affects the production of the vector. If the transduction of the non-frameshift vector in the test-cell (that lacks the blocking gene) causes cytoplasmic boiling, unusual chromatin condensation, or genomic fragmentation, then the deleterious gene causes apoptosis of the host cell.

The present inventive method and cells can be augmented by the use or application of peptide mimetic inhibitors of caspases. Peptide mimetics suitable for use in the context of the present invention include (1) acetyl-aspartyl-glutamyl-valinyl-aspartic aldehyde, (2) carbobenzoxy-L-aspartyl-α-(2,6 dichlorobenzoyl) methane (Z-Asp-CH$_2$-DCB), and (3) carbobenzoxy-valinyl-alaninyl-aspartyl methoxy-fluromethane (Z-VAD-FMK). Although these peptide mimetics are generally very expensive, especially when preparing commercial quantities of a viral eukaryotic gene transfer vector, addition of these mimetics to the medium of a host-production cell can decrease the cytotoxicity, cytostasis, or apoptosis of a host-production cell.

Advantageously, increased yields of viral eukaryotic gene transfer vectors comprising a deleterious gene can be augmented by adding one or more of these peptide mimetics to the medium of a host-production cell comprising a blocking gene. In yet another aspect of the present invention, these peptide mimetics or other small molecule inhibitors of apoptosis can be substituted entirely for the blocking gene. Of course, it will be appreciated that such compounds are presently prohibitively expensive, and for at least that reason the blocking gene is usually to be preferred to the small molecule inhibitors of apoptosis.

An embodiment of the present invention in which the viral eukaryotic gene transfer vector comprises a deleterious gene and a blocking gene can be illustrated by considering two adenoviruses. One exemplary adenovirus comprises a fully functional E1 region, a fully functional E3 region and an apoptosis-inducing gene (e.g., a FasL gene, a FADD gene, or a FLICE gene) in the E4 region. In this exemplary embodiment, the E1 gene products stimulate the expression of the adenoviral 14.7 K protein and the action of the 14.7 K adenoviral protein substantially counteracts the apoptotic effects of the Fas ligand and allows the efficient in vitro propagation of the vector. An alternative, but related, exemplary embodiment is an adenoviral vector comprising a crmA gene under the control of an exogenous (or heterologous) promoter and a FasL gene. In this embodiment, the presence and expression of the 14.7 K protein are optional, because the crmA protein substantially counteracts the apoptotic effects of the Fas ligand.

The present invention also provides an alternative method to obtain higher yields of desired viral gene transfer vectors. For example, higher yields of a eukaryotic gene transfer vector comprising a DNA segment encoding an inducible nitric oxide synthase (iNOS) can be obtained by delivering a dominant negative calmodulin variant (e.g., by transduction or transfection of the cell by a foreign gene encoding the variant) to a cell that is permissive for the replication of the viral eukaryotic gene transfer vector. Of course, it is often desirable for the cell to also comprise one or more essential gene functions of the vector so that the vector carrying the iNOS can be replication-deficient. For example, if the vector carrying the iNOS gene is an adenoviral vector that is deficient in at least one essential gene function of the E1 region of an adenovirus and comprises a DNA segment encoding an inducible nitric oxide synthase, then the host-production cell comprises the calmodulin variant and a DNA segment that complements the E1 deficiency.

Yet another embodiment of the present invention provides a eukaryotic cell for the production of a vector the carries a gene that encodes and expresses an iNOS gene. This embodiment of the inventive cell comprises a gene that encodes and overexpresses a polypeptide that binds to biopterin or calmodulin, preferably both, such that the polypeptide prevents the activation of the iNOS. This polypeptide can be a dominant negative nitric oxide synthase, preferably a dominant negative iNOS. It is also preferable that the polypeptide itself lacks nitric oxide synthase activity. For the purposes of the present invention, a dominant negative variant or mutant is a protein which (1) substantially or totally lacks an enzymatic or catalytic activity and (2) when co-expressed in a cell comprising a wild-type protein of the same type blocks the bulk of the activity (e.g., at least 80%, preferably at least 95%, of the activity of the wild-type protein). Preferably, both the measurement of inhibition of the activity of the wild-type protein and the use of the cell are under conditions such that the molar quantity of the dominant negative mutant is at least three times, preferably at least ten times, greater than the molar quantity of the wild-type protein.

EXAMPLES

The invention can be more clearly understood with reference to the following examples. The following examples further illustrate the present invention, but should not be construed as in any way limiting its scope.

Example 1

This example demonstrates that the expression of a blocking gene in a host-production cell that comprises a viral eukaryotic gene transfer vector comprising a deleterious gene advantageously increases the production of the viral eukaryotic gene transfer vector. This example also demonstrates that a cell line expressing the E1 region of an adenovirus and a blocking gene is sufficiently resistant to apoptosis, induced by the expression of the deleterious gene, to support an increased yield of a viral eukaryotic gene transfer vector carrying the deleterious gene.

The adenoviral vector AdFasL/G, as shown in FIG. 1, which is a schematic diagram of the generation of AdFasL/G, was constructed by homologous recombination on HEK-293 cells. AdFasL/G is an adenoviral vector (with deletions in the E1 and E3 regions) containing a dual expression cassette that expresses the murine FasL gene from the CMV promoter and a reporter gene, β-glucuronidase, from the Rous Sarcoma virus RSV) promoter. This dual expression cassette is inserted in the E1 region of the virus. AdFasL/G directs the expression of Fas ligand and, therefore, readily induces apoptosis in cells transduced with the vector.

Passage of the AdFasL/G stock on HEK-293 cells yielded no detectable virus in three out of four attempts. The fourth attempt resulted in a virus yield of about 20 pfu/cell. In contrast, as is detailed directly below, passage of the AdFasL/G stock on HEK-293 cells comprising the blocking gene crmA yielded significantly higher levels of virus, averaging in the range of about 600 to about 1200 pfu/cell.

HEK-293 cells were transduced with an adenoviral vector comprising a crmA gene under the control of a CMV promoter to provide a cell line useful in the context of the present invention that supports replication of E1-deficient adenoviruses comprising a deleterious gene. These cells were then transduced with AdFasL/G at a moderate or low multiplicity of infection (MOI) (in the present example, an MOI of 5).

The cells were examined 24 hrs after transduction by AdFasL/G and the level of apoptosis was undetectable. The level of AdFasL/G recovered was about 600 to 1200 pfu/cell. Thus, expression of a blocking gene, such as crmA, in host production cells, such as HEK-293 cells, enables the improved production of a viral eukaryotic gene transfer vector comprising a deleterious gene, such as the AdFasL/G vector, which comprises a deleterious gene that induces apoptosis.

Example 2

This example illustrates that a blocking gene can usefully increase the peak yield of viral eukaryotic gene transfer vectors comprising a deleterious gene, such as one that activates the caspase-3 pathway.

AdRAF 1–149, AdiNOS, AdΔIkB, and AdTAM67 are adenoviral vectors expressing the amino terminal 149 amino acids of RAF (a dominant negative version of RAF, which is an oncogene); iNOS (inducible nitric oxide synthase); ΔIkB (a deletion mutant of IkB (e.g., encoding amino acids 54 to 317; see also Brockman et al., *Mol. Cell Biol.*, 15, 2809 (1995)), which is constitutively active and substantially more stable than the wild type protein); and a Jun dominant negative variant (an oncogenic transcription factor), respectively. Additionally, AdFas, AdFADD and AdFLICE are adenoviral vectors expressing the Fas receptor, FADD and FLICE, respectively. Each of these proteins are well-known in the art and adenoviral vectors that direct their expression are difficult to make in reasonable quantities because of the deleterious effects attendant their expression in mammalian cells.

Individual cultures of the host-production cells are transduced with an adenoviral gene transfer vector encoding crmA and subsequently infected with each of the foregoing adenoviral vectors. After 48 hrs, the transduced cells are harvested and the yield of each adenoviral vector is measured. The yield of each adenoviral vector is expected to increase at least 5-fold over the yield obtained in the absence of crmA.

Example 3

This example demonstrates that blocking genes encoding crmA and adenoviral 14.7 K protein (of the E3 region) facilitate the production of an adenoviral vector comprising a deleterious gene in a host-production cell.

An adenoviral vector comprising the murine FasL gene, a deleterious gene, was propagated in HEK-293 cells ($10^6$ cell;) previously transfected with a plasmid (10 μg of plasmid was transfected by $CaPO_4$ co-precipitation): plasmid pAdCLxHBM does not express a transgene, i.e., a negative control; plasmid pAdCLxCrmA expresses crmA; plasmid pAd14.7/G expresses adenoviral 14.7 K protein under control of the CMV promoter; plasmid E1b19K expresses adenoviral 19 K protein; plasmid p50/p65 (NF-κB-1 and relA) expresses subunits of NF-κB; plasmid vHRas expresses the viral Harvey Ras oncoprotein; and plasmid BXB expresses activated RAF oncogene (Bruder et al., *Genes and Development*, 6, 545–556 (1992)). Cells were infected with AdFasL/G at an MOI of 5. Measurements were made 48 hrs after infection.

Figure 2:
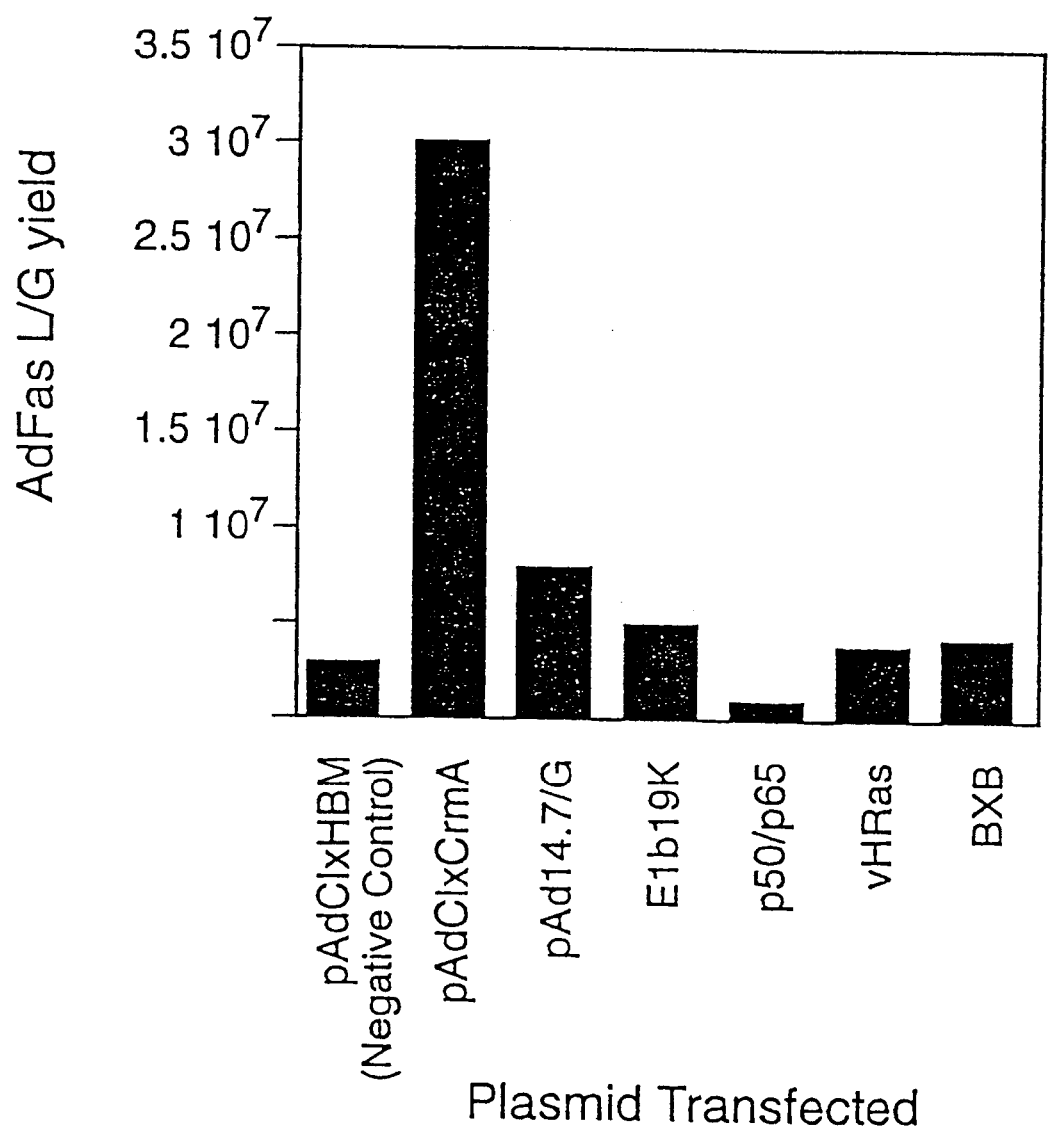
FIG. 2 is a bar graph of AdFasL/G yields when co-transfected with various plasmids.

The results are shown in FIG. 2, which is a bar graph of AdFasL/G yield for the various plasmids. Expression of the adenoviral 14.7 K protein and, particularly, crmA, increased the yield of the AdFasL/G viral vector approximately ten-fold.

Example 4

This example demonstrates that expression of crmA in HEK-293 cells increases the yield of an adenoviral vector comprising the iNOS gene.

Six independent HEK-293-derived cell lines having crmA under control of the CMV promoter (CMV-crmA expression cassettes) in their genomes (HEK-293/crmA cells) were isolated and characterized. CrmA production in each cell line was measured and found to vary by as much as 10-fold from cell line to cell line. An adenoviral vector having the iNOS gene in the E1 region, AdiNOS, was used to infect normal HEK-293 cells and each of the crmA expressing HEK-293 cell lines. Less than 25 infectious AdiNOS particles per cell were produced in the normal HEK-291 cells. In contrast, from about 100 to about 200 infectious AdiNOS particles per cell were produced on the HEK-293/crmA cells. No correlation between the level of crmA production and the yield of virus was observed, which indicates that the crmA level was saturating in all cells.

Example 5

This example demonstrates that adenoviral 14.7 K protein and crmA block apoptosis induced by Fas oligomerization, FADD and FLICE deleterious gene products.

HEK-293 cells and A549 cells were transiently transfected with three plasmids: one that expresses Green Fluorescent Protein (GFP); one that expresses FasL, FADD or FLICE, and one that expresses either 14.7 K protein or crmA protein. The expression of GFP in the cells makes it easy to assay the cells for apoptosis, which was measured about 12 hrs after transfection. FasL, of course, induces apoptosis through the Fas ligand receptor. Similarly, FADD and FLICE are well-known in the art to stimulate apoptosis.

Figure 3:
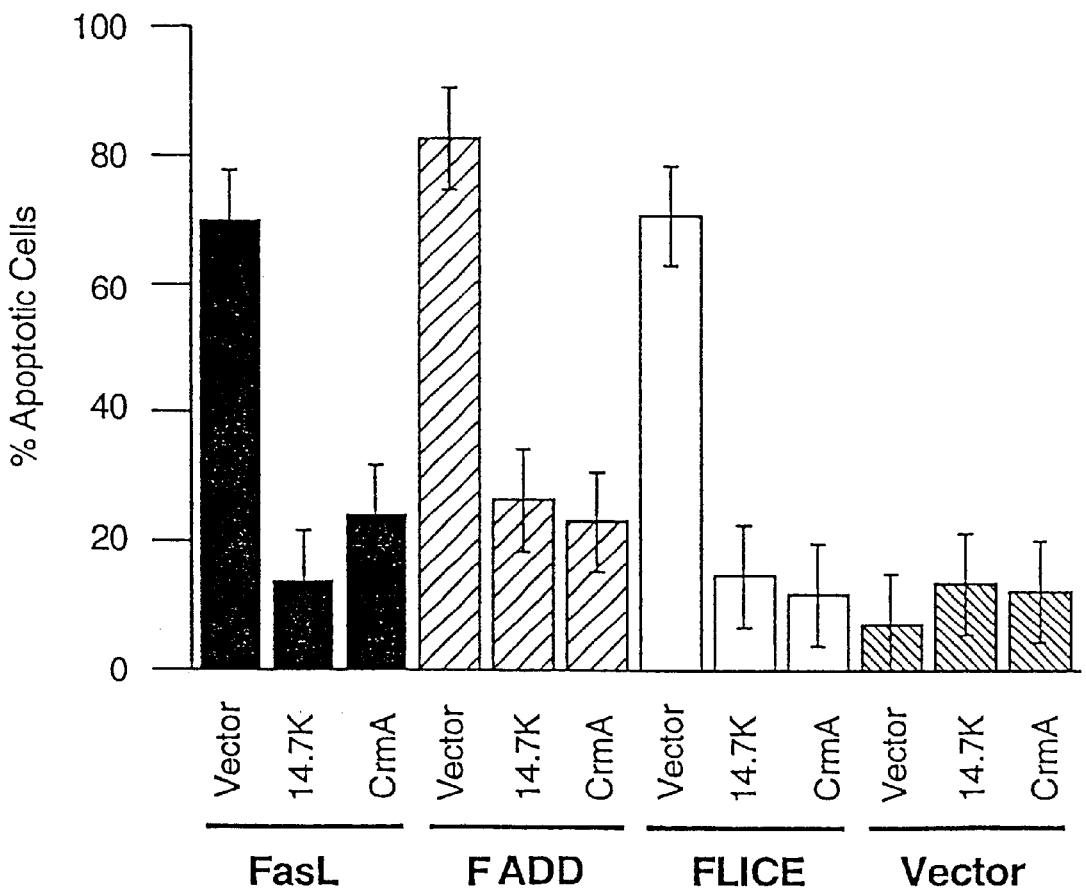
FIG. 3 is a bar graph of % apoptotic cells when various deleterious genes are co-transfected in HEK-293 cells expressing crmA or 14.7 K protein.
Figure 4:
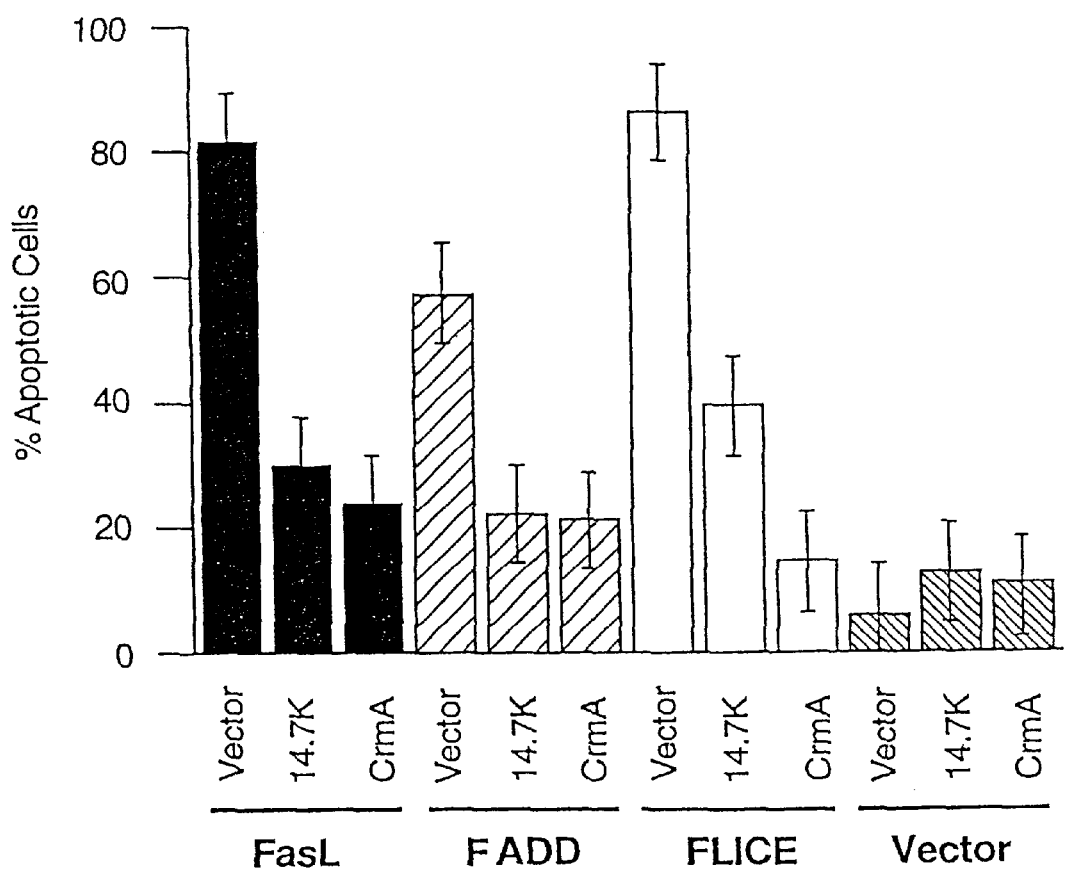
FIG. 4 is a bar graph of % apoptotic cells when various deleterious genes are co-transfected in A549 cells expressing crmA or 14.7 K protein.

The results are shown in FIGS. 3 and 4. FIG. 3 is a bar graph of % apoptotic HEK-293 cells when such cells are co-transfected with a deleterious gene and a gene encoding either crmA or 14.7 K protein compared to control cells. FIG. 4 is a bar graph of % apoptotic A549 cells when such cells are co-transfected with a deleterious gene and a crmA or 14.7 K protein-encoding gene compared to control cells. FIGS. 3 and 4 depict the ability of crmA and adenoviral 14.7 K protein to block the apoptotic action of FasL, FLICE and FADD on HEK-293 cells and A549 cells, respectively. As can be seen in FIG. 3, transfection of HEK-293 cells with the FasL, FLICE, or FADD expression vectors in the absence of crmA or 14.7 K expression results in the apoptosis of about 60–80% of the cells. However, co-transfection of HEK-293 cells with the CrmA or 14.7 K expression plasmids reduces the level of apoptosis to less than about 30% and, in some instances, to less than about 20%.

This example demonstrates that the expression of crmA and adenoviral 14.7 K can advantageously reduce the level of apoptosis in the host-production cell (e.g., HEK-293 cells or A549 cells), which can in turn allow for higher yields of viral eukaryotic gene transfer vectors comprising a deleterious gene.

Example 6

This example demonstrates that use of AE25 host-production cells, which do not contain the potential recombination region found in HEK-293 cells, reduces the levels of replication-competent adenoviral (RCA) particles produced when a deleterious gene product is serially passaged in the presence of a blocking gene product, such as an anti-apoptotic gene.

Although AdFasL/G (see Example 1, supra) yields obtained on HEK-293/crmA cells (see Example 4, supra) were substantially improved over those obtained on HEK-293 cells, the yields were still 10-fold lower than those achieved with non-toxic vectors and 100-fold less than that of a wild-type adenovirus infection on HEK-293 cells. Thus, wild-type virus have a considerable advantage over AdFasL/G. This selective advantage was realized when AdFasL/G was serially passaged on HEK-293/crmA cells. Three of the four large-scale preparations of AdFasL/G grown on HEK-293/crmA cells resulted in the generation of RCA levels of greater the 1 RCA unit in $10^5$ pfu of AdFasL/G.

To compensate, AE25 (an A549-based E1 complementation host-production cell line), which does not contain sequence identity with the AdFasL/G adenoviral gene transfer vector on the right side of the expression cassette, was utilized. AE25 cells expressing crmA (AE25/crmA cells) were infected with AdFasL/G. Virus titers obtained on these cells were increased by 100-fold compared to titers on AE25 cells. Growth of AdFasL/G on AE25/crmA cells has not resulted in detectable RCA generation after serial passage, demonstrating that this cell line is useful for the efficient production of pure preparations of AdFasL/G.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of propagating an adenoviral, herpes viral or adeno-associated viral vector comprising a deleterious gene in a eukaryotic host-production cell in vitro, which method comprises introducing the viral vector, comprising a deleterious gene, into a eukaryotic host-production cell comprising a blocking gene, said blocking gene encoding crmA, baculoviral p35 protein, an IAP gene product, or a FLIP gene product, whereupon said vector is propagated at a higher yield of vectors per cell in said eukaryotic host-production cell in the presence of said blocking gene than in the absence of said blocking gene.

2. The method of claim 1, wherein said blocking gene is incorporated into the genome of the eukaryotic host-production cell.

3. The method of claim 1, wherein said blocking gene is present on a plasmid or a vector.

4. The method of claim 1, wherein said eukaryotic host-production cell is mammalian.

5. The method of claim 1, wherein said yield of vectors per cell at its peak in the presence of said blocking gene is at least five times greater than the yield of vectors per cell at its peak in the absence of said blocking gene.

6. The method of claim 5, wherein said yield of vectors per cell at its peak in the presence of said blocking gene is at least twenty times greater than the yield of vectors per cell at its peak in the absence of said blocking gene.

7. The method of claim 1, wherein said eukaryotic host-production cell is HEK 293 or A549, wherein said A549 expresses the adenovirus type 2 early region I.

8. A method of propagating an adenoviral, herpes viral or adeno-associated viral vector in a eukaryotic host-production cell in vitro, which method comprises introducing into a eukaryotic host-production cell, the viral vector comprising a deleterious gene, and a blocking gene, said blocking gene encoding crmA, baculoviral p35 protein, an IAP gene product, or a FLIP gene product, whereupon said vector is propagated at a higher yield of vectors per cell in said eukaryotic host-production cell in the presence of said blocking gene than in the absence of said blocking gene.

9. The method of claim 8, wherein said blocking gene is present on a plasmid or a vector, wherein said vector is other than the adenoviral, herpes viral or adeno-associated viral vector.

10. The method of claim 8, wherein said blocking gene is present on the adenoviral, herpes viral or adeno-associated viral vector.

11. The method of claim 10, wherein said blocking gene is native to the virus from which the adenoviral, herpes viral or adeno-associated viral vector is obtained, and wherein the blocking gene (i) is operably linked to a heterologous promoter or (ii) is in a nonnative location on the vector.

12. The method of claim 8, wherein said eukaryotic host-production cell is mammalian.

13. The method of claim 8, wherein said yield of vectors per cell at its peak in the presence of said blocking gene is at least five times greater than the yield of vectors per cell at its peak in the absence of said blocking gene.

14. The method of claim 13, wherein said yield of vectors per cell at its peak in the presence of said blocking gene is at least twenty times greater than the yield of vectors per cell at its peak in the absence of said blocking gene.

15. The method of claim 8, wherein said eukaryotic host-production cell is HEK 293 or A549, wherein said A549 expresses the adenovirus type 2 early region I.

16. An adenoviral, herpes viral or adeno-associated viral vector, which (i) comprises a deleterious gene and (ii) comprises a blocking gene selected from the group of genes consisting of genes that encode crmA, baculoviral p35 protein, an IAP gene product, and a FLIP gene product.

17. A eukaryotic cell comprising an adenoviral, herpes viral, or adeno-associated viral vector of claim 16.

18. A eukaryotic cell comprising a blocking gene and an adenoviral gene transfer vector, wherein the adenoviral gene transfer vector comprises an adenoviral genome and a deleterious gene, and wherein said blocking gene either comprises a heterologous promoter or is present in a region of the adenoviral genome other than E3.

19. The eukaryotic cell of claim 18, wherein said blocking gene is present in the E1 or E4 region of the adenoviral genome.

20. The method of claim 1, wherein said blocking gene encodes crmA.

21. The method of claim 8, wherein said blocking gene encodes crmA.

22. The adenoviral, herpes viral or adeno-associated viral vector of claim 16, wherein said blocking gene encodes crmA.

23. A eukaryotic cell comprising an adenoviral, herpes viral, or adeno-associated viral vector of claim 22.

24. The eukaryotic cell of claim 18, wherein the blocking gene encodes crmA.

25. The eukaryotic cell of claim 21, wherein the blocking gene encodes crmA.

* * * * *